United States Patent [19]

Garman et al.

[11] 4,287,373

[45] Sep. 1, 1981

[54] PERBROMINATION OF PHENOL AND DIPHENYL ETHER AT ELEVATED TEMPERATURE USING BROMINE AS THE REACTION MEDIUM

[75] Inventors: John A. Garman; Rastko I. Mamuzic; Robert B. McDonald; John L. Sands, all of West Lafayette; Gregory Thompson, Battleground, all of Ind.

[73] Assignee: Great Lakes Chemical Corporation, West Lafayette, Ind.

[21] Appl. No.: 81,035

[22] Filed: Oct. 1, 1979

Related U.S. Application Data

[63] Continuation-in-part of Ser. No. 39,267, May 16, 1979, abandoned, which is a continuation of Ser. No. 858,653, Dec. 8, 1977, abandoned.

[51] Int. Cl.$^3$ ...................... C07C 41/22; C07C 37/62
[52] U.S. Cl. ..................................... 568/639; 568/776
[58] Field of Search ................................. 568/639, 776

[56] References Cited

U.S. PATENT DOCUMENTS

3,965,197  6/1976  Stepniczka ..................... 568/639 X

FOREIGN PATENT DOCUMENTS

1411524  10/1975  United Kingdom .

*Primary Examiner*—Bernard Helfin
*Attorney, Agent, or Firm*—Kirkland & Ellis

[57] ABSTRACT

A process for the perbromination of phenol and diphenyl ether by brominating the corresponding compound in bromine as the sole reaction medium using metal and metal-containing catalysts at an elevated initial reaction temperature of at least about 35° C., preferably at least about 45° C., substantially enhances reaction productivity without adversely affecting product yield or quality.

12 Claims, 2 Drawing Figures

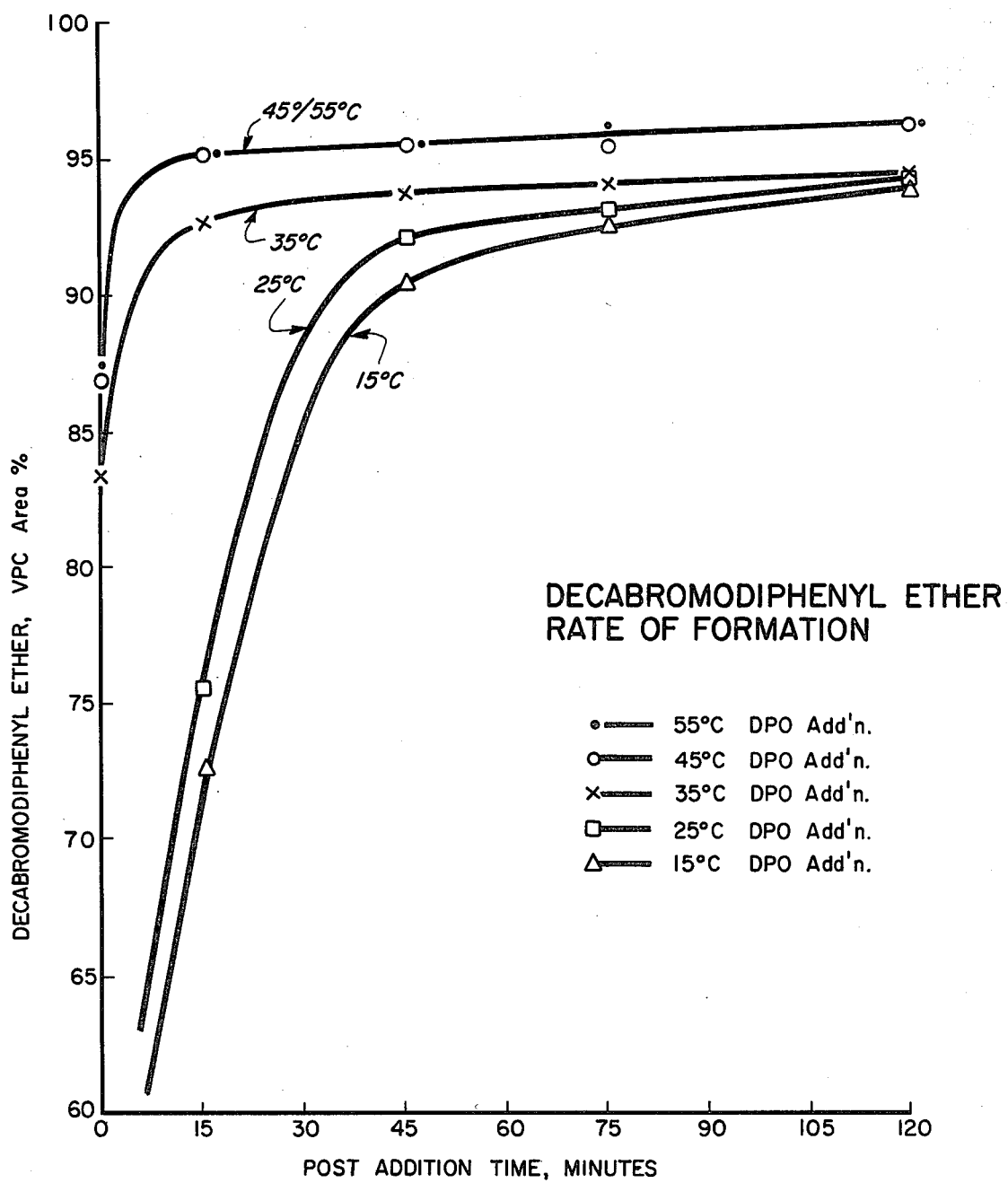

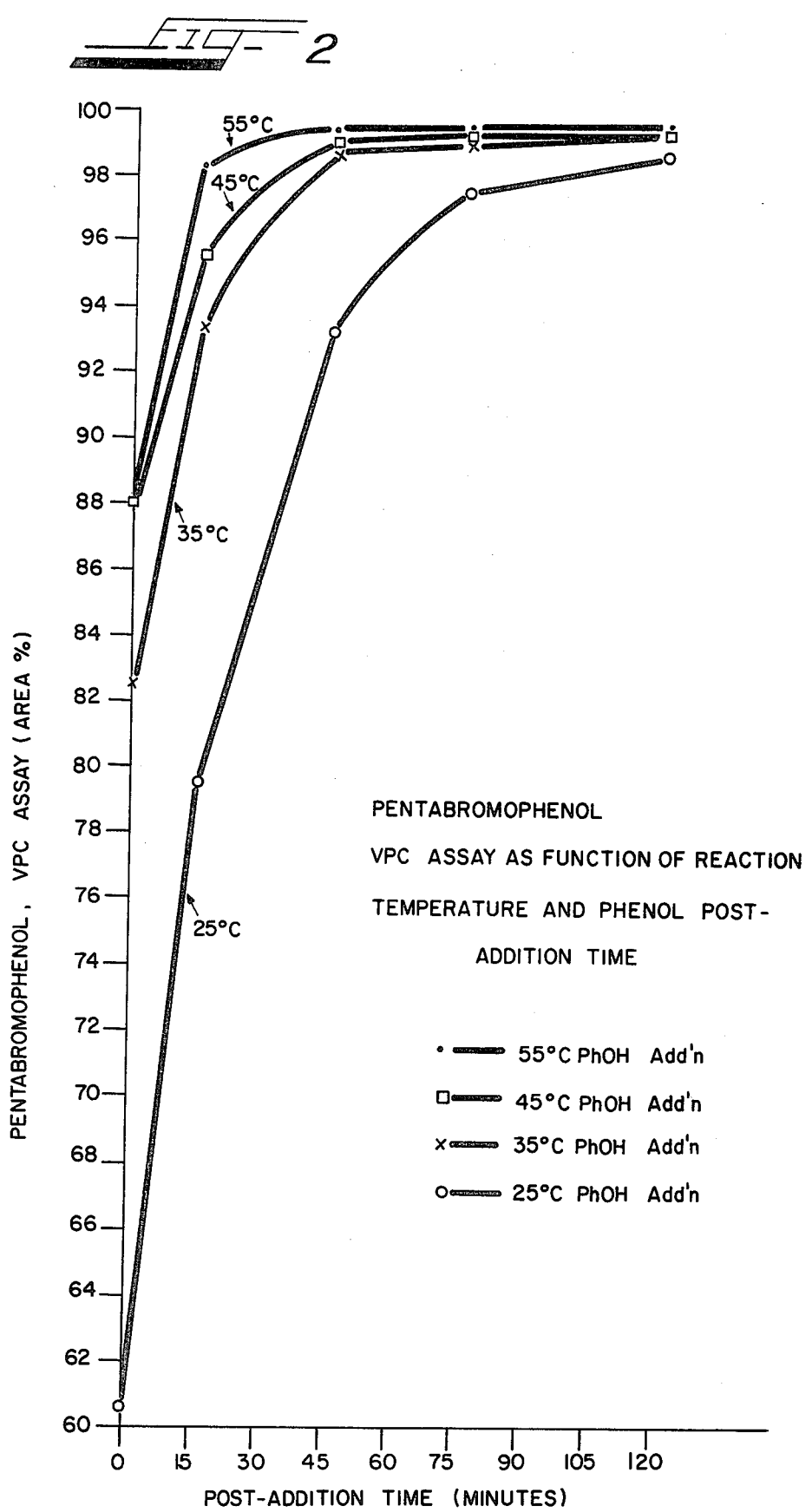

4,287,373

PERBROMINATION OF PHENOL AND DIPHENYL ETHER AT ELEVATED TEMPERATURE USING BROMINE AS THE REACTION MEDIUM

CROSS-REFERENCE

This application is a continuation-in-part of applicants' co-pending application Ser. No. 39,267, filed May 16, 1979, now abandoned, which in turn was a continuation of applicants' application Ser. No. 858,653, filed Dec. 8, 1977, now abandoned.

BACKGROUND OF THE INVENTION

1. Field of the Invention

This invention relates generally to a process for the perbromination of phenol and diphenyl ether by brominating the appropriate compounds at a temperature in excess of 35° C. in bromine as the sole reaction medium in the presence of selected catalysts.

2. Description of the Prior Art

In the past, numerous processes have been employed for replacing all the nuclear hydrogen atoms in aromatic compounds such as diphenyl ether and the like. None of these processes has been found to be entirely successful; all have been found to have disadvantages.

Prior art perbromination processes in general have involved use of an up to about 20% excess of bromine in the presence of various kinds of reaction media and solvents such as ethylene dibromide, carbon tetrachloride, chloroform, methylene bromide, acetylene tetrachloride, and the like depending on the particular aromatic compound to be brominated. Perbromination of aromatic compounds has also been carried out in reaction media such as oleum, concentrated sulfuric acid, fuming sulfuric acid, liquid sulfur dioxide, and the like.

Each of these process approaches has serious disadvantages for perbromination, especially for commercial operations. The use of halogenated organic solvents has disadvantages which include low productivities, undesirably slow reaction rates, and the necessity for recovery of the solvents for recycle. In some cases this technique results in the introduction of small but significant amounts of chlorine into the final product, thus limiting product quality. In addition a number of non-condensed aromatic compounds do not undergo perbromination satisfactorily under conditions which can readily be employed using halogenated organic solvents.

Disadvantages in the use of oleum as a reaction medium include, in addition to all the usual problems associated with its handling on a large scale, the required use of large volumes, thus reducing reactor productivity, difficulties in product isolation, disposal of large volumes of sulfuric acid, and poor quality products resulting from the presence of sulfur-containing contaminants such as brominated benzene-sulfonic acids. The latter contamination problem is also encountered in the use of liquid sulfur dioxide as reaction medium.

The inherent difficulties attendant on large scale perbromination are illustrated by several exotic synthetic chemical approaches proposed for hexabromobenzene. For example, the chemical literature describes the pyrolysis of octabromocyclohexenones and the reaction of hexabromocyclopentadiene with tribromoacetaldehyde at super-atmospheric pressures and highly elevated temperatures.

Another approach to the preparation of hexabromobenzene and other perbrominated aromatic compounds has been the use of bromine/chlorine mixtures as the bromination agent. This process suffers the serious disadvantage of introducing small but significant amounts of chlorine into the final products thus limiting their final quality.

Yet another process which has been described for the polybromination of aromatic compounds requires the use of powerful mechanical mixers to maintain partially brominated solid intermediates in a sufficiently fine state of subdivision to permit access of bromine liquid or vapor in attempts to achieve high levels of bromination.

It has also been proposed to prepare completely brominated derivatives of aromatic compounds containing one or more phenyl groups through the use of bromine solvent (100% excess or more) and a bromine transfer catalyst at relatively low reaction temperatures of from about 10° C. to ambient (i.e., about 20°–25° C.) A related process has involved ring bromination of aromatic compounds employing a minimum excess of 20% of bromine in the presence of halogenation catalysts at ambient (20°–25° C.) temperature. While these processes have, when carried to completion, permitted perbrominated product to be obtained in good yield, such results have been achieved only through acceptance of economic penalties. Inefficiencies introduced as a result of low reactor bromination temperatures make use of such processes on a commercial scale even less desirable.

Accordingly, it is an object of this invention to prepare pentabromophenol and decabromodiphenyl ether in high yield and purity by a relatively simple reaction using excess bromine as both reactant and the sole reaction medium.

Another object of the invention is to prepare perbrominated compounds of the character described substantially free from lower brominated products.

It is also an object to employ at least a 75% excess above the stoichiometric amount of bromine for the perbromination.

A further object is to carry out perbromination reactions of the character described at elevated temperatures in order to enhance significantly equipment productivities per unit volume and time without affecting product yield and qualities.

SUMMARY OF THE INVENTION

The foregoing and other objects, advantages, and features of the present invention may be achieved with substantially perbrominated phenol and diphenyl ether produced by reacting phenol or diphenyl ether at an elevated initial reaction temperature of from about 35° C. up to about 80° C. in the presence of an at least about 75% excess and not more than about 400% excess of the stoichiometric amount of bromine and a small but catalytically effective amount of a catalyst selected from the group consisting of iron, iron halides, iron compounds which form iron bromide under the conditions of the reaction, aluminum, aluminum halides and aluminum compounds which form aluminum bromide under the conditions of the reaction and continuing the reaction at an elevated temperature of from about 35° C. up to about 80° C. after addition of the reactants has been completed, while maintaining the excess of bromine in order to achieve substantial perbromination of the aromatic compound.

DESCRIPTION OF THE DRAWING

FIG. 1 is a plot of data demonstrating the criticality of the 35° C. minimum bromination temperature in the case of the perbromination of diphenyl ether.

FIG. 2 is a plot of data demonstrating the criticality of the 35° C. minimum bromination temperature in the case of the perbromination of phenol.

DESCRIPTION OF THE PREFERRED EMBODIMENTS

In accordance with this invention, substantially perbrominated phenol and diphenyl ether may be obtained by reacting such a compound in the presence of a substantial excess of bromine as both reactant and the sole reaction medium. Desirably, the bromine is present at an excess of at least 75% but not more than about 400%.

The reaction takes place in the presence of a small but catalytic amount of a bromination catalyst which may include iron and aluminum, their halides, and compounds which form iron or aluminum bromide under the conditions of the reaction.

It is especially important in accordance with this invention that the reaction take place at an elevated initial reaction temperature. The bromine reaction medium should be maintained at a temperature of at least about 35° C. and preferably at least about 45° C. up to about 80° C. before the addition of the phenol or diphenyl ether is initiated. The reaction medium is maintained at such an elevated reaction temperature throughout the addition of the aromatic compound and is thereafter maintained at an elevated temperature, preferably at reflux, after addition of the phenol or diphenyl ether is completed, while maintaining the excess of bromine.

Bromination of diphenyl ether and phenol employing excess bromine as the reaction medium proceeds much faster than does the bromination using an excess of bromine at ambient or lower temperatures yet product yield and quality are not adversely affected. The reaction time is even shorter when compared with reactions employing molar equivalents or even the usual slight bromine excess of up to 20% and an organic bromination solvent.

Isolation and purification of the perbrominated products obtained in the bromine reaction medium of this invention may be carried out in a variety of ways, and the required steps are considerably easier and simpler than for products made by conventional methods and in addition give higher yields of purer and more uniform products.

Using bromine as the reaction medium and elevated reaction temperatures, essentially quantitative yields of the perbrominated products containing only very small amounts of underbrominated materials are obtained.

The perbromination in bromine reaction carried out under the process of the invention proceeds in substantially identical fashion with substantially the same results using either fresh feed of the desired starting organic reactant or mixtures of its under-brominated by-products as may have been obtained in previous reactions as the starting reactants. For instance using either fresh diphenyl ether or partially brominated diphenyl ether as starting reactants substantially the same results are obtained. It is preferred in some cases that these by-products be subjected to some form of distillation or other purification before reuse.

Although the precise percentage excess of bromine over the stoichiometric amount required that is used as the reaction medium is not critical, bromine excesses of about 75% and up to and over 300% and to 400% have been found necessary. About a 100–200% excess has been found to be the optimum and preferred level for perbromination of phenol and diphenyl ether.

Bromination in a large excess of bromine in the range of about 100% to 200% excess gives more homogeneous and more highly brominated reaction products, whereas using smaller excesses of bromine (i.e., less than 75% excess) gives lower reaction rates, prolonged reaction times, and results in lumpy and more or less impure reaction products containing underbrominated material (i.e., incomplete bromination.)

Typical experiments using the process of the invention may be carried out using both "dry" bromine (i.e. regular bromine containing up to about 15 ppm of water) and so-called "wet" bromine (i.e., bromine containing more than about 15 ppm water.) The former so-called dry bromine is preferred for use in carrying out the bromination reactions (i.e. as the bromination agent and sole reaction medium). Wet bromine has been found to have several detrimental effects in the reaction.

The reaction proceeds much more slowly when wet bromine is used, the degree of slowness being more or less directly related to the amount of water present. In addition the reaction products obtained even after prolonged reaction times are more or less underbrominated (that is, not all available nuclear hydrogen atoms are replaced by bromine), the degree of replacement more or less depending on the quantity of water present.

The presence of water also increases the amount of bromination catalyst needed to a level substantially above the normal optimum levels.

As noted, an essential parameter of the process of this invention is that the bromination reaction of the phenol or diphenyl ether using excess bromine as the reaction medium be initiated at elevated temperatures substantially in excess of ambient (i.e., 20°–25° C.) temperatures; that is, the reaction is initiated at temperatures in excess of about 35° C. up to about 80° C., preferably at a temperature of about from 45° C. up to about 60° C.

After addition of the phenol or diphenyl ether has been completed, the temperature may be advantageously increased further to reflux levels during later stages of the bromination. In the case of the perbromination of phenol, typical reflux temperatures of 60°–64° C. are observed, whereas in the case of perbromination of diphenyl ether, reflux occurs at about 59°–60° C.

Significant advantages accrue with the use of elevated initial reaction temperatures as high as practical within the specified range. The solubilities of products and/or partially brominated intermediates are substantially increased by operating at higher temperatures that are substantially above room temperature. This increased solubility effect gives products of higher assay in any given reaction time resulting in higher equipment productivities. Thus, to assure completion of the perbromination reaction at the highest efficiency it is desirable to use reaction mixture temperatures as high as may be permitted by the reaction mixture composition, which temperatures, depending on composition of the mixture, may exceed significantly the boiling point of the bromine contained therein and may in some instances be as high as 80° C. or more where superatmospheric pressures are employed.

Substantial benefits are achieved by operating at temperatures in the upper part of this range, including higher yields together with higher assays of desired products. Surprisingly, the reaction may be successfully carried out at elevated initial reaction temperatures without adversely affecting desired product quality objectives.

In properly designed production facilities, operating at temperatures above 35° C., preferably at about 45°-55° C., the bromination cycle is reduced, product assay increases, reactor productivity per unit time significantly increases, and substantial commercial advantages are achieved. If desired, it is also possible to operate the perbromination at temperatures substantially above the boiling point of the mixture by use of superatmospheric pressure.

A total reaction time of from 1 to 100 hours, dependent primarily on the organic reactant, has been found to be adequate for complete reaction under the conditions of the invention to convert quantitatively the starting materials to perbrominated products in which substantially all replaceable nuclear hydrogen atoms have been replaced by bromine using bromine as the sole reaction medium (perbromination). This time period has been used entirely satisfactorily both for laboratory and larger scale runs. In general, a total reaction time of up to about 20 hours was found to be sufficient to produce high yields of high assay products in the experiments studied. In some cases, perbromination is found to be complete in three hours or less. There is nothing critical about the period of addition employed for the aromatic compound. It is desirable to add the aromatic compound at a sufficiently slow rate to minimize loss of reactants overhead and to permit the desired elevated reaction temperature to be maintained under conditions of control and safety.

The order of addition of the reactants (i.e., the aromatic compound to be brominated and bromine) may be varied somewhat as desired, and no method appears to be unduly critical. However, in order to achieve the full advantages of the invention for preparation of the perbrominated compounds, the required excess of bromine should be present in the reactor during the latter stages of the bromination. For best results, the stoichiometric excess of 75% up to 400% bromine preferably should be present during the last half of the reaction.

The more normal and preferred procedure is the slow addition of phenol or diphenyl ether to the excess of bromine which functions as the reaction medium as well as the brominating agent, at the same time controlling the temperature to the desired elevated temperature by cooling or heating as required. It is desirable, however, to add the aromatic compound feed reactant at a sufficiently slow rate to minimize loss of bromine, volatile reaction products, and lower-brominated intermediates overhead.

A modification of the foregoing preferred method of adding the aromatic compound to the total bromine charge may also be used advantageously to increase productivity of the reactor. The modification consists of initially introducing a part of the total bromine into the reactor and thereafter adding the aromatic compound described above. As the bromination proceeds, the volume of the reaction mass decreases, and, as this decrease occurs, the remaining portion of the total excess bromine is added.

It is also possible to carry out the process of the invention by addition of the bromine to the phenol or diphenyl ether, preferably in liquid form. It is an advantage of this method of addition that the bromine is introduced into the reaction mixture as it reacts, which also results in a reaction mixture of decreased volume and thus in increased productivity. A disadvantage of this procedure is that a relatively large amount of the reactant is exposed to bromine, and the bromination reaction is much more difficult to control. Thus, the chance for overheating of the reaction mixture is considerably increased over the other methods of reactant contact. This can result, if uncontrolled, in overhead loss of bromine, organic reactant, and volatile brominated products. A further disadvantage is that the reaction mixture may pass through a solid or semi-solid stage with attendant stirring difficulties.

As noted, the bromination in bromine process of this invention can be advantageously employed using phenol or diphenyl ether as the starting reactants.

A number of different forms of metal-containing catalysts have been tested. The catalysts which have been found most effective are either based on iron or aluminum as the metallic component. Those found useful include, for example, metallic iron, iron bromide, iron chloride, metallic aluminum, aluminum chloride and aluminum bromide.

Iron and iron compounds which form iron bromide under the conditions of the reaction have been found to be the catalysts of choice for preparation of pentabromophenol by bromination of phenol in a bromine reaction medium. Thus, iron powder employed as the catalyst gives the highest yield of perbrominated product having the highest assay. The iron powder is also found to remain active throughout the entire bromination period. Iron bromide (ferric bromide) and iron chloride (ferric chloride) have also been found to be quite satisfactory. Ferric bromide appears to give a slightly faster initial bromination than does iron powder. However, it has the disadvantage of giving product which shows slightly lower assay of desired product. Iron chloride as catalyst was slightly less effective than iron powder and iron bromide and may give perbrominated products slightly contaminated with chlorine. Aluminum chloride was somewhat less active than iron and gave products of somewhat lower assay. It also tends to be inactivated more quickly than iron in the course of the brominations thus requiring introduction of additional portions of the catalyst during the reaction (bromination) period. Aluminum chloride does, however, have the advantage that it is colorless and therefore does not add color to the products. For final perbrominated products whose purity requirements are not chemical purity, use of aluminum chloride permits elimination of a purification step, or at least a simplified purification.

Aluminum and aluminum compounds which form aluminum bromide under conditions of the bromination reaction have been found to be the catalysts of choice for preparation of decabromodiphenyl ether by bromination in a bromine reaction medium. Aluminum metal, for example in the form of foil or powder, believed to be converted rapidly under conditions of the reaction to aluminum bromide, was found to be an efficient catalyst for the bromination process. Frequently, however, it is found more convenient to use as catalyst preformed anhydrous aluminum bromide or aluminum chloride. In certain of these instances aluminum bromide or aluminum chloride results in somewhat more rapid brominations and/or more complete perbrominations when used as catalysts for the bromination. A further advantage noted for aluminum, aluminum halides and aluminum compounds which form aluminum bromide under conditions of the bromination reaction is that these catalyst species are colorless and do not add color to the final products if allowed to remain therein, so that in final products in which purity requirements are not those of chemical purity use of aluminum compounds permits elimination or simplification of the purification step. Metallic iron, iron halides, and compounds which form iron halides under reaction conditions may also be employed in the perbromination of diphenyl ether.

The required amount of catalyst, i.e., the iron, iron compound, aluminum or aluminum compound, calculated as the metal, has been found to be a small but catalytically effective amount for perbromination and may vary from about 0.1% to about 10% of metal based on the weight of organic substrate as reactant. Amounts of catalyst up to 15% by weight or more based on the metal are considered satisfactory but economically impractical. It has been demonstrated, however, that within the above limits relatively larger amounts of metal catalyst are required under certain special conditions, for instance, if "wet" (i.e., watercontaining) bromine is used. Large quantities of catalyst may be used where aluminum and iron halides are added as the catalytic material.

The reaction mixtures resulting from carrying out the process of the invention using bromine as the perbromination reaction medium and an elevated initial reaction temperature can be processed by a variety of work-up procedures to isolate the perbrominated products. The crude reaction mixture, which may contain the brominated products, excess bromine reaction medium, and excess catalyst, can, for instance, be subjected to stripping either at atmospheric pressure or preferably under reduced pressure at about 80° C. to the point of constant weight of the residue. The crude product which is thus isolated may be further purified, for instance, by digestion with methanol, ethylene dibromide, or dilute hydrochloric acid. This isolation method by stripping is fast, simple and gives reliable yield data and relatively pure product. It has the disadvantage that it may leave residual metal-containing catalyst in the product.

It is also possible to isolate the perbromination product by replacing the excess bromine in the reaction mixture with water followed by filtration of the aqueous reaction mixture. The crude product obtained may then be purified by relatively simple digestion procedures as described above. This isolation procedure may cause production and/or engineering problems in large scale operations.

It is also possible to replace the excess bromine in the reaction mixture by ethylene dibromide followed by filtration. The crude product can then be further purified by digestion procedures as described above.

In one preferred variation of the isolation step, the entire reaction mixture is transferred into hot acidified water with simultaneous volatilization of the excess bromine followed by filtration of the aqueous mixture. Purification by digestion with suitable organic solvents may then be used as described above. In carrying out this process, the excess bromine flashes out almost immediately after contact with the hot water, disintegrating the solid perbrominated product particles and increasing their effective contact surface, meanwhile dissolving any residual catalyst. After bromine removal is completed, the crude reaction product is isolated by filtration.

This method has numerous advantages. These include removal of the greater portion of the residual catalyst and the ready recovery of the excess bromine for reuse after drying.

It is also possible to carry out a further variation of the latter isolation step in which the isolation and purification steps are essentially combined. Operating thus, the aqueous product is not filtered but is contacted directly with a waterimmiscible organic solvent. The product becomes concentrated in the organic phase from which the aqueous phase is then removed thus separating the catalyst from the product. The product can then be isolated from the organic phase and purified by known means.

In general, organic solvents which can be employed in isolation, digestion and/or purification steps include the lower molecular weight alkanols, such as methanol, ethanol, the propanols, and the butanols, lower molecular weight halogenated compounds, such as ethylene dibromide, chlorobenzene, chloroform, acetylene tetrachloride and carbon tetrachloride, and ketones such as acetone and other suitable solvents.

Perbrominated products which result from use of this bromination in bromine reaction are decabromodiphenyl ether and pentabromophenol.

It is generally possible to predict the product(s) which will result from application of this perbromination process under optimum reaction conditions to any particular starting material. The general rule is that every nuclear hydrogen atom will be replaced by a bromine atom if the reaction is carried to completion, that is, until the evolution of hydrogen bromide has stopped. This level of bromination can be reached by proper adjustment of reaction temperature, catalyst concentration and reaction time. The perbromination process is continued until such time as the sampling indicates that the desired degree of bromination has been reached. Or the bromination reaction may be continued until evolution of hydrogen bromide has substantially ceased. Continuation of the bromination and extension of reaction periods beyond the point of bromination desired serves no useful purpose and may lead in some cases to degradation of products, fragmentation of the organic materials, and formation of tarry or resinous by-products.

Among the advantages of the elevated temperature bromination process of this invention are the obtaining of substantially quantitative yields of crude perbrominated products of relatively high purity. The very small amounts of impurities which may be present are metal catalysts and metallic catalyst compounds and minor amounts of lower brominated products of the organic reactant which may, if desired, be recycled as reactants for further perbromination.

Surprisingly, the advantages of initiating the reaction at elevated temperatures as disclosed herein is quite specific to phenol and diphenyl ether, and similiar benefits are not observed with other noncondensed aromatic compounds such as toluene and xylenes.

The process shows high productivity (i.e., there is high product quantity per unit of reactor volume employed.) The process also has been found to make possible the easy production of perbrominated phenol and diphenyl ether which heretofore were commercially impractical or only available by more difficult and/or complicated synthetic methods and from special equipment. The reaction conditions employed in carrying out the invention are relatively mild and require only simple equipment, important economic and safety factors in plant operations. The bromination reactions proceed much faster when bromine is the reaction medium as compared to the rate when using other solvents, both organic and inorganic, such as fuming sulfuric acid.

Since both the thermal stability and the color of the perbrominated products are important factors for flame retardants, the production of these perbrominated derivatives in relatively pure state offers great advantages for their end use in flame retardant compositions. The availability and purity of the products are also important for their use as chemical intermediates for instance for the production of possible pesticides and drugs.

Any partially brominated by-products which may be produced can readily be recovered and recycled for complete perbromination in the same process and equipment.

Processing, isolation and purification procedures are flexible in a number of ways. As is described herein, in combination with the disclosed elevated initial reaction temperature, there are a number of procedural steps which may be varied in contacting the reactants, the bromine reaction medium and catalysts, in isolating the products, and in purifying the products, proper combination of which produces good results.

The following examples are presented as illustrative only of the process of the invention and in no way are intended to limit the invention as the specific features of the process described.

EXAMPLES

EXAMPLE 1

Decabromodiphenyl Ether

A 1 liter four neck round bottom flask was fitted with a mechanical stirrer, a double walled reflux condenser, sample removal tube, thermometer, and reagent addition tube. The flask was vented to a water trap for collection of by-product hydrogen bromide. Dry bromine, 1164 g. (7.26 moles, 150% excess), was charged into the reaction flask, followed by 250 mg. of 20 mesh aluminum (0.0093 mole). The mixture was stirred for 15 minutes, during which time the aluminum was fully converted into the aluminum bromide.

Vessel temperature was controlled within plus or minus 1° C. by employing a Therm-O-Watch temperature regulator (Model L7/800, available from Instruments for Research and Industry, Cheltenham, Pa. 19012) in combination with a Jack-O-Matic (Model JOM-3 also available from Instruments for Research and Industry).

The bromine-catalyst mixture in the vessel was warmed to 35° C., and addition of diphenyl ether, 49.5 g. (0.29 mole), was initiated at a constant rate by means of a syringe pump over a period of about 51 minutes. The reaction temperature was held at 35° C. plus or minus 1° C. throughout the diphenyl ether addition. Additional heat was applied after diphenyl ether addition had been completed, and the reaction temperature increased to about 59° C. within about 20 minutes. After about 120 minutes of post addition heating, 300 ml. of water was added to the reaction slurry, the reflux condenser, sample removal tube, and reagent addition tubing were removed. A distilling head with thermometer, a condenser, and a receiver were attached to one flask joint, and excess bromine was distilled off until a temperature of 100° C. was achieved.

Decabromodiphenyl ether was filtered from the aqueous slurry, washed with water and dried at 110° C. in a forced air oven.

Vapor phase chromatographic ("VPC") analysis of the resulting product showed decabromodiphenyl ether 94.7 area percent, nonabromodiphenyl ether isomers totaling 4.5%, and octabromodiphenyl ether isomers totalling 0.5%.

EXAMPLE 2

Decabromodiphenyl Ether

The procedure of Example 1 was repeated except that the bromine-catalyst mixture was heated to a temperature of 45° C. plus or minus 1° C. prior to initiation of diphenyl ether addition and was maintained at such temperature throughout the diphenyl ether addition.

Vapor phase chromatographic analysis of the resulting product showed decabromodiphenyl ether 96.4 area percent, nonabromodiphenyl ether 3.2%, and octabromodiphenyl ether 0.4%.

EXAMPLE 3

Decabromodiphenyl Ether

The procedure of Example 1 was followed except that initial temperature of the bromine-catalyst mixture was raised to 55° C. plus or minus 1° C. prior to diphenyl oxide addition and was maintained at that temperature until diphenyl ether addition was completed. About five minutes after application of post addition heat, the reflux temperature of 59° C. was achieved.

Vapor phase chromatographic analysis of the resulting product showed 96.3% decabromodiphenyl ether, 3.3% nonabromodiphenyl ether and 0.3% octabromodiphenyl ether.

EXAMPLE 4

Pentabromophenol

The bromination of phenol was carried out in a reaction apparatus consisting of a reaction vessel equipped with a dropping funnel, stirrer, thermometer, and a water-cooled condenser connected to a water trap. Into the reaction flask 1198.7 g. (7.5 moles; 150% excess) of bromine and 0.57 g. of iron powder were charged. Phenol (56.7 g.; 0.6 moles) was added dropwise from the dropping funnel with stirring over a period of 100 minutes. During this period the reaction temperature was controlled at approximately 46°–47° C.

After addition of phenol was completed, the reaction mixture was warmed to reflux temperature (about 60°–64° C.), and the reaction was allowed to continue until evolution of HBr ceased. The total reaction time was 3 hours.

The reaction mixture was cooled to approximately 50° C. and transferred into 328 ml. of aqueous hydrobromic acid. The excess bromine was distilled out under atmospheric pressure over a period of 2.5 hours. The suspension was cooled to room temperature, filtered, and the solid reaction product was washed with water and dried. The crude product was obtained in the form of a cream colored solid, melting at 229.9° C. (lit. 229.5° C.), having a VPC assay of 99.6%. The yield of the crude product was substantially quantitative.

EXPERIMENTAL EVALUATIONS

A study was conducted in order to determine the effect of diphenyl ether addition temperature on reaction productivity and decabromodiphenyl ether yield and quality. The experimental results were obtained by monitoring the vapor phase chromatography (VPC) area percent assay of brominated product as a function of diphenyl ether addition temperature and post addition reflux time.

In the preparations described in Examples 1-3, reaction mixture samples were withdrawn at the conclusion of diphenyl ether addition, at 15 minutes, 45 minutes, 75 minutes and 120 minutes following diphenyl ether addition.

The withdrawn samples were analyzed by vapor phase chromatography (VPC) by dissolving at least one gram of each in dibromomethane or dibromoethane in a ratio of 1 gram of sample to 40 milliliters of solvent and employing a HP 5754 instrument with flame ionization detector and a 2 millimeter ID×4 ft. glass column packed with 3% Dexsil 300 on 100/120 mesh Supelcoport at a temperature 200°-340° C. programmed at 10° C. per minute.

For comparative purposes, similar runs were conducted at diphenyl ether addition temperatures of 15° C. plus or minus 1° C. and 25° C. plus or minus 1° C., respectively, with samples being withdrawn and analyzed at the same post addition time intervals.

Table I records decabromodiphenyl ether assay (VPC area percent) as a function of diphenyl ether addition temperature and post addition reflux time.

TABLE 1

| Initial Diphenyl Ether Addition Temperature | 15° C. | 25° C. | 35° C. | 45° C. | 55° C. |
|---|---|---|---|---|---|
| Time post diphenyl (Min.) ether addition | Decabromodiphenyl Ether VPC Assay (Area %) | | | | |
| 0 | 31.9 | 35.5 | 83.4 | 86.9 | 87.2 |
| 15 | 73.0 | 75.5 | 92.8 | 95.2 | 95.1 |
| 45 | 90.5 | 92.2 | 93.8 | 95.6 | 95.7 |
| 75 | 92.8 | 93.2 | 94.1 | 95.4 | 96.2 |
| 120 | 94.1 | 94.6 | 94.7 | 96.4 | 96.3 |

An inspection of the data in Table I reveals that at ambient diphenyl ether addition temperatures of 15° and 25° C., an undesirably slow rate of product formation is observed, requiring a full two hours of post addition refluxing to attain the minimally desired 94% decabromodiphenyl ether assay. In sharp contrast, for reactions conducted at 45° C. and at 55° C., essentially identical results are achieved, with assay levels of 95% being achieved after only 15 minutes of refluxing (i.e., after only ⅛th as long.)

At the 35° C. diphenyl ether addition level (representing the minimum addition temperature that can be employed while achieving the benefits of this invention), a somewhat longer period is required (about 75 minutes) but still well short of the two hour period required in the case of the ambient temperature runs.

FIG. 1 plots the data of Table 1 and demonstrates in graphic form the formation rate of decabromodiphenyl ether as a function of diphenyl ether ("DPO") addition temperature and post addition reflux time. The 45° C. and 55° C. rate curves are identical and indicate the rapid rate of product formation occuring at those reaction temperatures. The rate curve for 35° C. describes a slightly slower reaction but nonetheless substantially faster than the unacceptably slow rates resulting from diphenyl ether additions at ambient conditions or lower (i.e., 15° C. and 25° C.)

By employing the initial elevated reaction temperatures of this invention in perbrominating diphenyl ether, post addition heating may be reduced by 75% or more without adversely affecting product yield or quality, thereby significantly enhancing reaction utility and productivity.

A further study demonstrates that the advantages of high temperature operation are achieved very selectively. Runs conducted at 25°, 35°, 45°, and 55° C. for each of phenol, toluene and p-xylene show not only that it is highly desirable to perbrominate phenol at elevated initial reaction temperatures, but also that it is undesirable to do so in the cases of toluene and p-xylene.

The following general procedure was employed for each run. The substrate to be brominated (toluene, p-xylene, and phenol) was added dropwise to an excess of bromine (300% over theoretical quantity needed for ring-perbromination) and iron catalyst (1% w/w on substrate) at specified temperature (25°, 35°, 45°, and 55° C.) over a period of 1 hour. After addition of the substrate was completed, the reaction mixture was stirred at the specified temperature for another 2 hours. Sampling of reaction mixture for VPC analysis was done immediately after addition of the substrate was completed (0 minutes) and 15, 45, 75, and 120 minutes thereafter.

The results of these runs are summarized as follows. In the case of pentabromophenol, elevated initial reaction temperature was found to have a highly beneficial effect. The highest assay (99.4%) of the desired perbrominated product was obtained at the highest reaction temperature 55° C. The reaction was also fastest at the highest temperature. Data observed in the phenol runs are reported in Table 2, and these data are also plotted in FIG. 2, which shows the rate of formation of pentabromophenol.

TABLE 2

| Initial Phenol Addition Temperature | 25° C. | 35° C. | 45° C. | 55° C. |
|---|---|---|---|---|
| Post Phenol Addition Time (Min.) | Pentabromophenol VPC Assay (Area %) | | | |
| 0 | 60.6 | 82.6 | 88.0 | 88.3 |
| 15 | 79.5 | 93.4 | 95.5 | 98.2 |
| 45 | 93.2 | 98.6 | 99.0 | 99.3 |
| 75 | 97.5 | 98.9 | 99.2 | 99.3 |
| 120 | 98.5 | 99.2 | 99.2 | 99.4 |

As these data reveal, an undesirably slow rate of formation of pentabromophenol is observed at ambient starting temperatures (25° C.). At that starting temperature, a period of two (2) hours of post addition time is required to achieve a product assay of 98.5%. A significantly shorter period of post addition heating (35-45 minutes) is needed where the reaction is initiated at 35° and 45° C., only about 30-40% of the time required at ambient temperature. Where 55° C. is the starting temperature, only 15 minutes of post addition heating, just ⅛ of that required at ambient temperature, is required to reach a product assay of 98.2%.

These findings are graphically shown in FIG. 2 which reveals that the elevated temperature (35°, 45°, and 55° C.) runs as a group significantly differ from the ambient (25° C.) temperature run.

Tables 3 and 4 contain the data for the toluene and p-xylene runs. In each case they demonstrate that, unlike diphenyl ether and phenol, the highest assays are observed at ambient (i.e., 25° C.) temperatures and the elevated initial reaction temperatures actually have a deleterious effect on the reaction.

TABLE 3

| Initial Toluene Addition Temperature | 25° C. | 35° C. | 45° C. | 55° C. |
|---|---|---|---|---|
| Post Toluene Addition Time (Min.) | \multicolumn{4}{c}{Pentabromotoluene VPC Assay (Area %)} | | | |
| 0 | 94.0 | 88.2 | 84.6 | 84.3 |
| 15 | 91.0 | 90.2 | 85.7 | 84.5 |
| 45 | 92.5 | 91.0 | 84.8 | 86.7 |
| 75 | 93.0 | 90.9 | 87.3 | 87.7 |
| 120 | 93.0 | 91.7 | 85.1 | 88.0 |

TABLE 4

| Initial p-Xylene Addition Temperature | 25° C. | 35° C. | 45° C. | 55° C. |
|---|---|---|---|---|
| Post p-Xylene Addition Time (Min.) | \multicolumn{4}{c}{Tetrabromo-p-Xylene VPC Assay (Area %)} | | | |
| 0 | 91.1 | 93.0 | 91.5 | 90.1 |
| 15 | 94.8 | 92.9 | 91.1 | 90.9 |
| 45 | 95.6 | 93.3 | 91.9 | 91.1 |
| 75 | 95.4 | 93.6 | 93.0 | 92.0 |
| 120 | 95.7 | 93.9 | 93.9 | 92.1 |

As the foregoing data reveal, with diphenyl ether and phenol alone of the noncondensed aromatic compounds evaluated, it is highly advantageous in terms of product yield and equipment productivity to employ elevated initial reaction temperatures (i.e., 35° C. or greater) that substantially exceed ambient conditions (i.e. about 25° C. or less.)

We claim:

1. A process for substantially perbrominating an aromatic compound selected from the group consisting of phenol and diphenyl ether comprising the steps of:
   adding the aromatic compound at an elevated initial temperature of from about 35° C. up to about 55° C. to a mixture of:
   at least a 75% excess and not more than about a 400% excess of the stoichiometric amount of bromine; and
   a small but catalytically effective amount of a catalyst selected from the group consisting of iron, iron halides, iron compounds which form iron bromides under the conditions of the reaction, aluminum, aluminum halides, and aluminum compounds which form aluminum bromide under the conditions of the reaction; and
   continuing the reaction at an elevated temperature at which reflux can occur after addition of the aromatic compound has been completed while maintaining the excess of bromine in order to achieve substantial perbromination of the aromatic compound.

2. A process, as claimed in claim 1, in which the reaction is initially carried out at a temperature of from about 45° C. up to about 55° C.

3. A process, as claimed in claim 1, in which the excess of bromine is about 100% to about 200% of the stoichiometric amount for perbromination of the aromatic compound.

4. A process, as claimed in claim 1, in which the catalyst is present in an amount of from about 0.1% to about 10% by weight, based on the metal equivalent weight relative to the amount of the aromatic compound.

5. A process for substantially perbrominating diphenyl ether comprising the steps of:
   adding diphenyl ether at an elevated initial temperature of from about 35° C. up to about 55° C. to a mixture of:
   at least a 75% excess and not more than about a 400% excess of the stoichiometric amount of bromine; and
   a small but catalytically effective amount of a catalyst selected from the group consisting of iron, iron halides, iron compounds which form iron bromides under the conditions of the reaction, aluminum, aluminum halides, and aluminum compounds which form aluminum bromide under the conditions of the reaction; and
   continuing the reaction at an elevated temperature at which reflux can occur after addition of the diphenyl ether has been completed while maintaining the excess of bromine in order to achieve substantial perbromination of the diphenyl ether.

6. A process, as claimed in claim 5, in which the reaction is initially carried out at a temperature of from about 45° C. up to about 55° C.

7. A process, as claimed in claim 5, in which the excess of bromine is about 100% to about 200% of the stoichiometric amount for perbromination of the diphenyl ether.

8. A process, as claimed in claim 5, in which the catalyst is present in an amount of from about 0.1% to about 10% by weight, based on the metal equivalent weight relative to the amount of the diphenyl ether.

9. A process for substantially perbrominating phenol comprising the steps of:
   adding phenol at an elevated initial temperature of from about 35° C. up to about 55° C. to a mixture of:
   at least a 75% excess and not more than about a 400% excess of the stoichiometric amount of bromine; and
   a small but catalytically effective amount of a catalyst selected from the group consisting of iron, iron halides, iron compounds which form iron bromides under the conditions of the reaction, aluminum, aluminum halides, and aluminum compounds which form aluminum bromide under the conditions of the reaction; and
   continuing the reaction at an elevated temperature at which reflux can occur after addition of the phenol has been completed while maintaining the excess of bromine in order to achieve substantial perbromination of the phenol.

10. A process, as claimed in claim 9, in which the reaction is initially carried out at a temperature of from about 45° C. up to about 55° C.

11. A process, as claimed in claim 9, in which the excess of bromine is about 100% to about 200% of the stoichiometric amount for perbromination of the phenol.

12. A process, as claimed in claim 9, in which the catalyst is present in an amount of from about 0.1% to about 10% by weight, based on the metal equivalent weight relative to the amount of the phenol.

* * * * *